(12) United States Patent
Nishiwaki et al.

(10) Patent No.: US 11,647,936 B2
(45) Date of Patent: May 16, 2023

(54) ELECTROENCEPHALOGRAM ELECTRODE

(71) Applicant: NIHON KOHDEN CORPORATION, Tokyo (JP)

(72) Inventors: Shigehiro Nishiwaki, Tokyo (JP); Junji Kuroda, Tokyo (JP); Mitsushi Hyogo, Tokyo (JP); Takayuki Mogi, Tokyo (JP); Kaoru Imajo, Tokyo (JP); Satoru Uchinuma, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 151 days.

(21) Appl. No.: 15/552,646

(22) PCT Filed: Feb. 15, 2016

(86) PCT No.: PCT/JP2016/000774
§ 371 (c)(1),
(2) Date: Aug. 22, 2017

(87) PCT Pub. No.: WO2016/136182
PCT Pub. Date: Sep. 1, 2016

(65) Prior Publication Data
US 2018/0028089 A1      Feb. 1, 2018

(30) Foreign Application Priority Data
Feb. 23, 2015   (JP) .............................. JP2015-032384

(51) Int. Cl.
*A61B 5/24*        (2021.01)
*A61B 5/00*        (2006.01)
(Continued)

(52) U.S. Cl.
CPC .............. *A61B 5/291* (2021.01); *A61B 5/369* (2021.01); *A61B 5/6803* (2013.01);
(Continued)

(58) Field of Classification Search
CPC ... A61B 5/0476; A61B 5/0478; A61B 5/6803; A61B 5/6814; A61B 5/6843;
(Continued)

(56) References Cited

U.S. PATENT DOCUMENTS 2,660,175 A  *  11/1953   Clydee .................. A61B 5/274
                                                     600/387
3,976,055 A  *   8/1976   Monter .................. A61B 5/276
                                                     600/394
(Continued)

FOREIGN PATENT DOCUMENTS

CN      201194799 Y      2/2009
CN      102379695 A      3/2012
(Continued)

OTHER PUBLICATIONS

Communication dated Aug. 21, 2018, issued by the Japanese Patent Office in counterpart Japanese Patent Application No. 2015-032384.
(Continued)

*Primary Examiner* — Adam Z Minchella
(74) *Attorney, Agent, or Firm* — Sughrue Mion, PLLC (57) ABSTRACT

An electroencephalogram electrode includes: a bottom portion on which a connection member is placed, the connection member which is configured to supply a biological signal that is acquired from a subject through conductive gel, to an external apparatus; an annular wall which annularly extends from the bottom portion in a contact direction with respect to the subject; and a plurality of barb members which are disposed in a holding space for the conductive gel that is located inside the annular wall, and which elongate from the bottom portion in the contact direction with respect to the subject.

20 Claims, 12 Drawing Sheets

(51) Int. Cl.
*A61B 5/291* (2021.01)
*A61B 5/369* (2021.01)

(52) U.S. Cl.
CPC .......... *A61B 5/6814* (2013.01); *A61B 5/6843* (2013.01); *A61B 2562/0215* (2017.08); *A61B 2562/0247* (2013.01); *A61B 2562/04* (2013.01)

(58) Field of Classification Search
CPC .... A61B 2562/0209; A61B 2562/0247; A61B 2562/04; A61B 2562/0215; A61B 5/251; A61B 5/291; A61B 5/252; A61B 5/6834; A61B 5/6835
See application file for complete search history.

(56) References Cited

U.S. PATENT DOCUMENTS

| | | | |
|---|---|---|---|
| 4,526,176 A | 7/1985 | Bremer et al. | |
| 4,693,711 A | 9/1987 | Bremer et al. | |
| 5,305,746 A | 4/1994 | Fendrock | |
| 5,722,404 A | 3/1998 | Lundback | |
| 6,201,982 B1 * | 3/2001 | Menkes | A61B 5/411 600/386 |
| 6,640,122 B2 * | 10/2003 | Manoli | 600/383 |
| 7,551,952 B2 * | 6/2009 | Gevins | A61B 5/0478 600/383 |
| 2002/0029005 A1 * | 3/2002 | Levendowski | A61B 5/6804 600/545 |
| 2004/0030258 A1 * | 2/2004 | Williams | A61B 5/061 600/544 |
| 2009/0082648 A1 * | 3/2009 | Ward | A61B 5/6834 600/309 |
| 2014/0012123 A1 | 1/2014 | Guger et al. | |
| 2014/0018658 A1 | 1/2014 | Karo et al. | |
| 2014/0081116 A1 * | 3/2014 | Nakashima | A61B 5/291 600/383 |
| 2016/0113542 A1 | 4/2016 | Guger et al. | |
| 2017/0027466 A1 * | 2/2017 | Kerth | A61B 5/0478 |
| 2017/0251947 A1 | 9/2017 | Guger et al. | |
| 2018/0235502 A1 * | 8/2018 | Nishimura | A61B 5/04085 |

FOREIGN PATENT DOCUMENTS

| | | |
|---|---|---|
| CN | 102512163 A | 6/2012 |
| CN | 103654772 A | 3/2014 |
| JP | 58-116338 A | 7/1983 |
| JP | 3-39008 U | 4/1991 |
| JP | 3-233303 A | 10/1991 |
| JP | 7-501738 A | 2/1995 |
| JP | 9-508830 A | 9/1997 |
| JP | 2006-271659 A | 10/2006 |
| JP | 2010-246751 A | 11/2010 |
| JP | 2012-183302 A | 9/2012 |
| JP | 2012-217721 A | 11/2012 |
| JP | 2012-239517 A | 12/2012 |
| JP | 2014-512211 A | 5/2014 |
| JP | 2015-221137 A | 12/2015 |
| WO | 00/45701 A1 | 8/2000 |
| WO | 2008109699 A2 | 9/2008 |
| WO | 2014/025353 A1 | 2/2014 |

OTHER PUBLICATIONS

Search Report dated May 6, 2016 issued by the International Searching Authority in counterpart International Application PCT/JP2016/000774 (PCT/ISA/210).

Written Opinion dated May 6, 2016 issued by the International Searching Authority in counterpart International Application PCT/JP2016/000774 (PCT/ISA/237).

Office Action dated Jun. 7, 2018 by the Japanese Patent Office in counterpart Japanese Patent Application No. 2015-032384.

Communication dated Sep. 11, 2019, from the State Intellectual Property Office of People's Republic of China in counterpart Application No. 201680011724.3.

Communication dated Jan. 6, 2021, from the State Intellectual Property Office of People's Republic of English China in counterpart Application No. 201680011724.3.

* cited by examiner

ELECTROENCEPHALOGRAM ELECTRODE

TECHNICAL FIELD

The present invention relates to an electroencephalogram electrode.

BACKGROUND ART

An electroencephalogram is an electrical signal which is generated by the brain activity of a human being. An apparatus for measuring an electroencephalogram measures an electroencephalogram by using electroencephalogram electrodes which are attached to the scalp of the subject. The measured electroencephalogram is varied depending on the position of the scalp. Therefore, the doctor or the like attaches electroencephalogram electrodes to predetermined positions of the scalp, and then measures an electroencephalogram. In an electroencephalogram measurement, namely, many electroencephalogram electrodes must be attached to respective predetermined positions of the scalp. The International 10/20 system shows an example of electrode placement.

Recently, it is expected that an electroencephalogram is used not only in a diagnosis in the field of brain function test, but also in that in the field of emergency medicine. Moreover, there is a high requirement for performing an electroencephalogram measurement for a long period of time. In order to meet such requests, a novel electroencephalogram electrode has been proposed.

PTL 1 discloses a quick-placement electroencephalogram electrode which can be quickly applied to the scalp. The electroencephalogram electrode has a plurality of tine sections 74 for gripping the hair. A sponge 20 impregnated with gel is placed in a space surrounded by the plurality of tine sections. The sponge is interposed between the scalp of the subject and an electrode metal. Therefore, the conductivity between the scalp of the subject and the electrode metal is ensured. According to the configuration in which the plurality of tine sections are disposed, reduction of the gel during the measurement can be avoided (PTL 1, FIG. 14, lines 46 to 60 of column 2).

CITATION LIST

Patent Literature

[PTL 1] U.S. Pat. No. 6,201,982

SUMMARY OF INVENTION

Technical Problem

In the electroencephalogram electrode of PTL 1, the sponge is impregnated with the gel, and hence the gel content is limited. In the electroencephalogram electrode of PTL 1 therefore, the gel dries, and it is difficult to stably perform an electroencephalogram measurement for a long period of time. Consequently, it is required to develop an electroencephalogram electrode having a structure in which gel itself can be held between the scalp of the subject and an electrode metal for a long period of time.

The invention has been conducted in view of the above-discussed situations. It is an object of the invention to provide an electroencephalogram electrode in which gel itself can be held at a predetermined position for a long period of time.

Solution to Problem

According to an aspect of the invention, there is provided an electroencephalogram electrode comprising: a bottom portion on which a connection member is placed, the connection member which is configured to supply a biological signal that is acquired from a subject through conductive gel, to an external apparatus; an annular wall which annularly extends from the bottom portion in a contact direction with respect to the subject; and a plurality of barb members which are disposed in a holding space for the conductive gel that is located inside the annular wall, and which elongate from the bottom portion in the contact direction with respect to the subject.

DESCRIPTION OF EMBODIMENTS

Embodiment 1

Hereinafter, embodiments of the invention will be described with reference to the drawings. In the drawings described in the specification, in order to make the drawings easily readable, the illustration may be sometimes adequately simplified, or the scale and position of a part of components may be different from those of the actual specifications.

Figure 1:
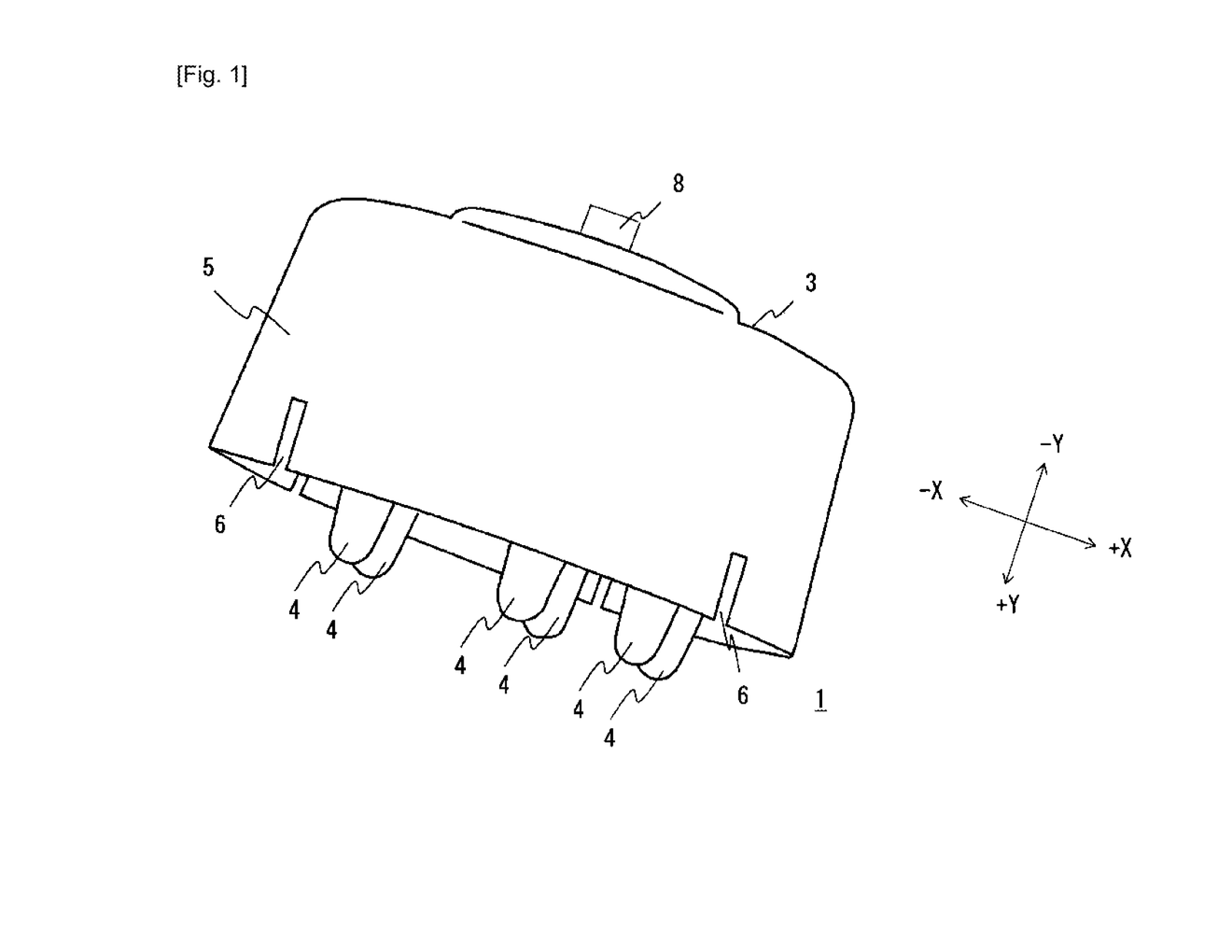
FIG. 1 is a perspective view showing the appearance of an electroencephalogram electrode 1 of Embodiment 1.

FIG. 1 is a perspective view of an electroencephalogram electrode 1 of Embodiment 1. The +Y direction shown in FIG. 1 approximately coincides with the direction in which the electrode is in contact with the scalp of the subject (hereinafter, the direction is referred to as the approximate contact direction).

The electroencephalogram electrode 1 has: a connection member 8 which is convex in the −Y direction; a bottom portion 3 on which an electrode metal 2 and the connection member 8 are placed; a plurality of barb members 4 which elongate from the bottom portion 3 in the +Y direction (approximate contact direction with respect to the subject); and an annular wall 5 which is annularly disposed on the bottom portion 3.

The annular wall 5 is not limited to have a cylindrical shape such as shown in FIG. 1, and may have an angular shape. Although not illustrated, the inside of the annular wall 5 is filled with conductive gel 7 (described later) for ensuring the conductivity between the electrode metal 2 and the head of the subject. Therefore, the annular wall 5 functions as a wall for preventing the conductive gel 7 from flowing out of the electroencephalogram electrode 1 to the outside.

The elongation direction of the barb members 4 may be directed in a direction which approximately coincides with the +Y direction (approximate contact direction with respect to the subject), and the members may not always elongate so as to be in contact with the scalp of the subject substantially perpendicularly. Similarly, the elongation direction of the annular wall 5 may be directed in a direction which approximately coincides with the +Y direction (approximate contact direction with respect to the subject).

A plurality of slits 6 which elongate from the +Y direction (approximate contact direction with respect to the subject) toward the bottom portion 3 are disposed in the annular wall 5. The electroencephalogram electrode 1 is attached to the scalp so as to be pressed toward the +Y direction. The disposition of the slits 6 allows the annular wall 5 to easily bend toward the outside. When the annular wall 5 bends in this way, the physical distance between the electrode metal 2 and the head of the subject is reduced, and therefore the electrode metal 2 can correctly acquire a biological signal of the subject. Since the bending occurs, it is possible to relax the pressure which is applied to the head of the subject by the annular wall 5.

The electroencephalogram electrode 1 has a size of about 2 cm in width (length in the X-axis direction) and about 1.5 cm in height (length in the Y-axis direction). The size is a mere example, and may be larger (or smaller) than these dimensions.

Figure 2:
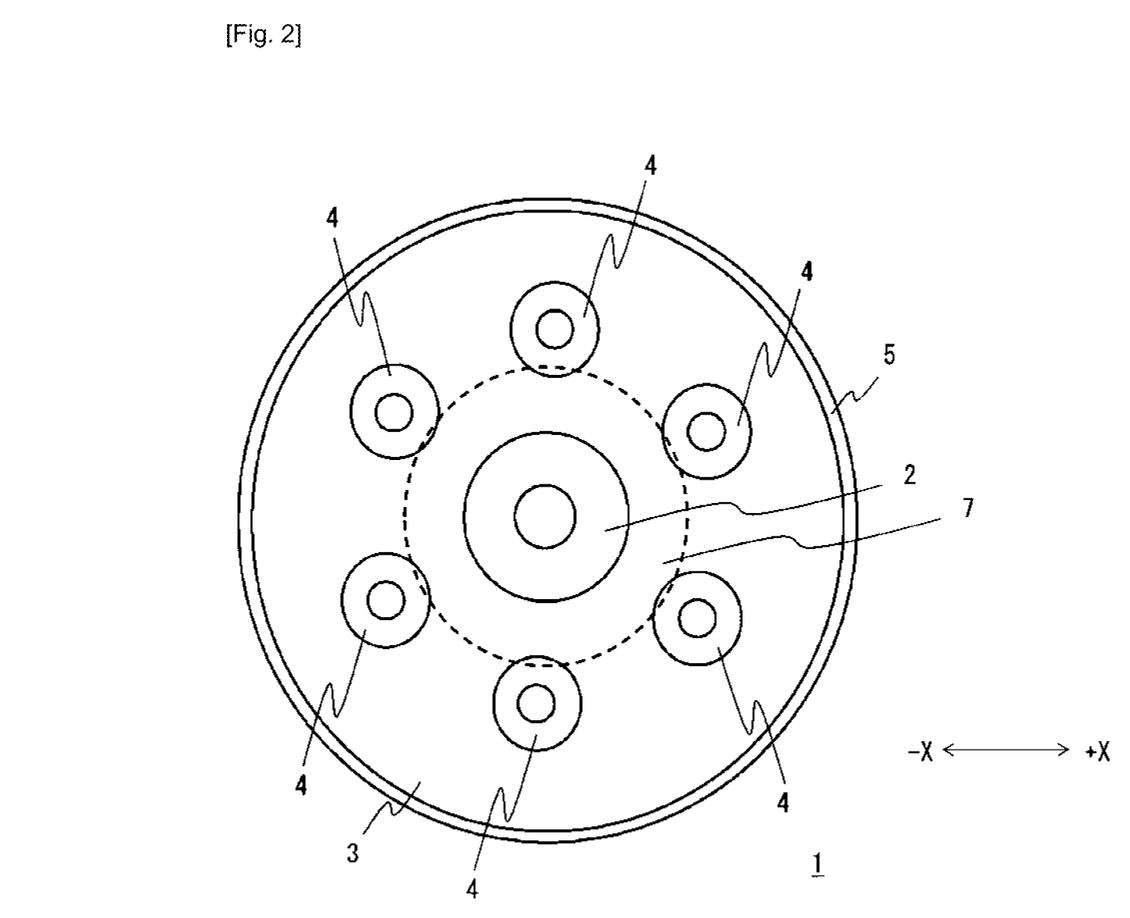
FIG. 2 is a bottom plan view of the electroencephalogram electrode 1 of Embodiment 1.

FIG. 2 is a diagram of the electroencephalogram electrode 1 as viewed from the +Y direction toward the −Y direction. In the embodiment, six barb members 4 are disposed. The conductive gel 7 is placed so as to be interposed among the barb members 4. That is, the conductive gel 7 is placed between the scalp of the subject and the electrode metal 2, and fixed by the barb members 4.

Figure 3:
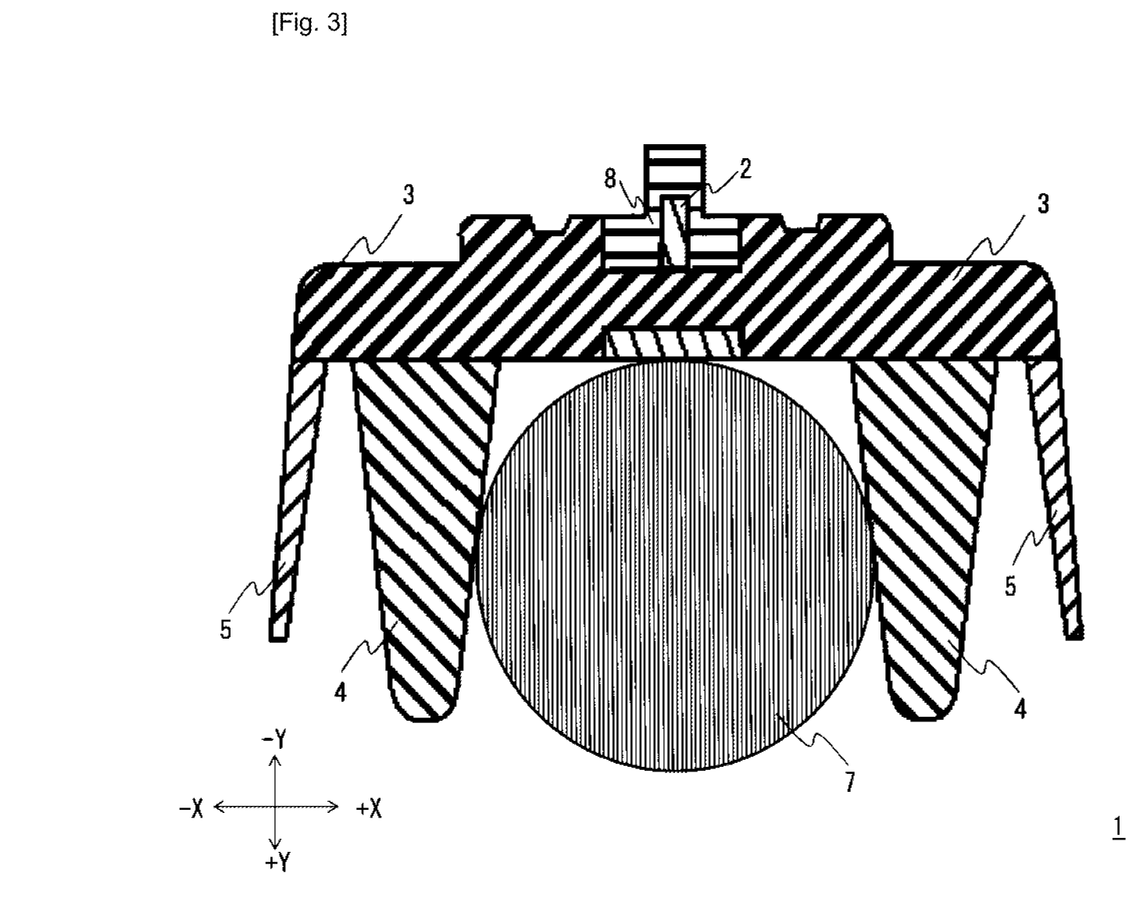
FIG. 3 is a sectional view of the electroencephalogram electrode 1 of Embodiment 1.

The configuration of the electroencephalogram electrode 1 will be described in more detail with reference to FIG. 3. FIG. 3 is a sectional view of the electroencephalogram electrode 1. As illustrated, the electrode metal 2 is placed in the vicinity of the middle of the bottom portion 3. In the electrode metal 2, the connection member 8 which is to be connected to an external apparatus (for example, an electrocardiograph) is convex in the −Y direction. A crocodile clip or the like which is attached to the tip end of a cable of the electrocardiograph is to be connected to the connection member 8. Namely, the connection member 8 is used for supplying a biological signal of the subject to the external apparatus (for example, an electrocardiograph). The electrode metal 2 is an electrode for acquiring a biological signal (electroencephalogram signal) of the subject, and may be a silver/silver chloride electrode or the like. In the example of FIG. 3, a through hole (not shown) is formed in the bottom portion 3, and the convex portion of the electrode metal 2 is passed through the through hole. The convex portion which has been passed through is fitted into a recess of the connection member 8, whereby the bottom portion 3, the connection member 8, and the electrode metal 2 are connected to one another (in other words, the connection member 8 and the electrode metal 2 are placed in the bottom portion 3).

The barb members 4 elongate from the bottom portion 3 toward the contact direction with respect to the subject (+Y direction). Preferably, portions of the barb members 4 which are to be in contact with the subject may be rounded so as not to pain the head of the subject. The barb members 4 have a hardness which can cause the barb members 4 to bend when the members are in contact with the head of the subject, and which can push the hair of the subject aside. Also the annular wall 5 has a hardness which can cause the wall to bend when the wall is in contact with the head of the subject.

In each of the barb members 4, preferably, the height (width from the −Y direction to +Y direction) is larger than the height (width from the −Y direction to +Y direction) of the annular wall 5. According to the configuration, the tip ends of the barb members 4 first push the hair of the subject aside, and then the annular wall 5 and the conductive gel 7 are in contact with the head of the subject. Since the barb members 4 push the hair aside, the electroencephalogram electrode 1 can be easily in close contact with the head of the subject.

As shown in FIG. 3, preferably, each of the barb members 4 is configured so that the diameter is smaller (tapered) as more moving from the −Y direction toward the +Y direction. That is, the barb members 4 have a shape which is tapered as more moving in the approximate contact direction with respect to the subject (+Y direction). According to the configuration, the pressure acting on the scalp is scattered, and the burden on the subject can be reduced.

Preferably, the annular wall 5 has a shape which is outward flared as illustrated. That is, the annular wall 5 is preferably extended while slightly shifting from the +Y direction toward the +/−X direction. According to the configuration, when the electroencephalogram electrode 1 is contacted with the head of the subject, the contacted portion can easily bend. The bending can lessen the pain which is caused by the contact of the annular wall 5 with the head of the subject. The materials of the bottom portion 3, the barb members 4, and the annular wall 5 will be described later.

The conductive gel 7 is placed in a holding space which is surrounded by the annular wall 5 and the barb members 4. The conductive gel 7 is a material for ensuring the conductivity between the electrode metal 2 and the head of the subject, and preferably has a high conductivity. Since the conductive gel 7 is placed in the holding space surrounded by the barb members 4, the gel does not drop toward the head (+Y direction) of the subject. In other words, the barb members 4 exert an effect of holding the conductive gel 7 in a hooking manner.

Alternatively, the conductive gel 7 may be placed so as to be filled in the internal space surrounded by the annular wall 5. Also in the alternative, the barb members 4 fix the conductive gel 7 in a hooking manner (prevent the gel from dropping), and the annular wall 5 prevents the conductive gel 7 from flowing toward the outside.

For example, the conductive gel 7 may be produced by mixing a highly conductive liquid (saline solution or the like) with a thickener. As a thickener, for example, alginic acid may be used. The viscosity of the conductive gel 7 is secured by adjusting the mixing ratio of the thickener. Even when the electroencephalogram electrode 1 is to be attached, therefore, it is possible to avoid a situation where the conductive gel 7 drops on the head of the subject, from occurring.

The electroencephalogram electrode 1 is connected to an electrocardiograph which is not shown. For example, the convex portion of the electrode metal 2 is connected to a cord end in which a crocodile clip is disposed at the tip end, and the cord is connected to the electrocardiograph. A plurality of electroencephalogram electrodes 1 are used to be placed respectively at positions of the head which are defined in the International 10/20 system. Then, the electrocardiograph measures the electroencephalogram of the subject.

In order to clarify the description, the bottom portion 3, the barb members 4, and the annular wall 5 have been described with reference to FIG. 3 as distinguished from one another. Actually, however, the electrode structure is not limited to this. The bottom portion 3, the barb members 4, and the annular wall 5 may be integrally formed. That is, the bottom portion 3, the barb members 4, and the annular wall 5 may be formed by the same material into an integral member.

Figure 4:
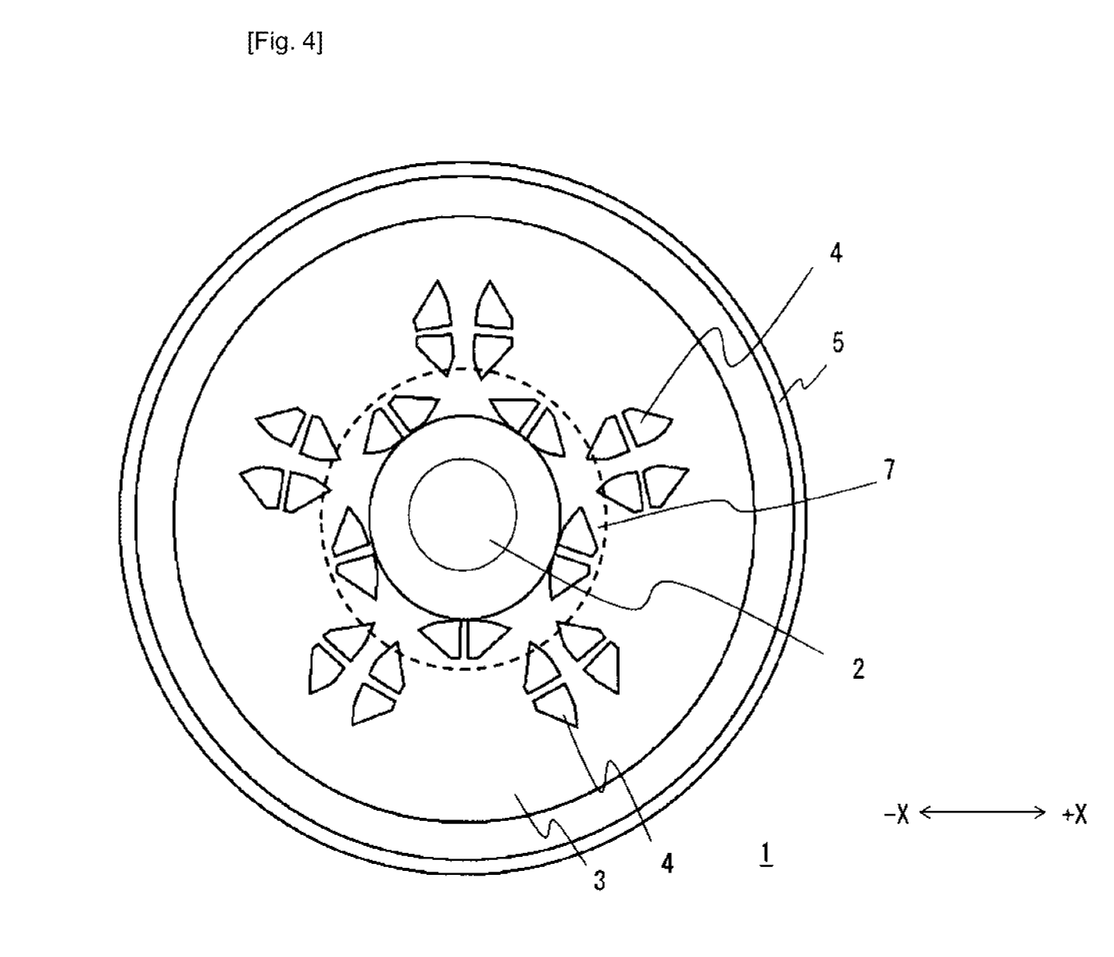
FIG. 4 is a bottom plan view of the electroencephalogram electrode 1 of Embodiment 1.

Although the example of FIG. 2 has been described while assuming that the six barb members 4 are disposed on the bottom portion 3, this structure is not essential. FIG. 4 is a view showing a modification of the electroencephalogram electrode 1. Similarly with FIG. 2, FIG. 4 is a diagram of the electroencephalogram electrode 1 as viewed from the +Y direction toward the −Y direction. In the modification, many barb members 4 which have a smaller diameter as compared with the case of FIG. 2 are placed. Also in this configuration, the conductive gel 7 can be held by the barb members 4. In other words, the conductive gel 7 is hooked by the barb members 4, and therefore can be prevented from dropping.

Referring again to FIG. 1, the material configurations of the bottom portion 3, the barb members 4, and the annular wall 5 will be described. As a first configuration method, it is contemplated that the bottom portion 3, the barb members 4, and the annular wall 5 are configured by a non-conductive material. The non-conductive material may be, for example, elastomer, more specifically polypropylene, or the like. When these members are configured by a non-conductive material, a biological signal of the subject is transmitted only through the conductive gel 7 to the electrode metal 2. Therefore, the electrode metal 2 can acquire a biological signal in which the influence of noise is reduced.

As a second configuration method, it is contemplated that the bottom portion 3, the barb members 4, and the annular wall 5 are configured as conductive members. For example, the bottom portion 3, the barb members 4, and the annular wall 5 may be made of a conductive carbon resin. According to the configuration, even when the conductive gel 7 dries up or becomes reduced, the electrode metal 2 can acquire a biological signal of the subject.

Alternatively, the bottom portion 3, the barb members 4, and the annular wall 5 may be made of a material which is produced by mixing a conductive carbon resin with silver or silver/silver chloride powder. According to the configuration, the conductivities of the bottom portion 3, the barb members 4, and the annular wall 5 can be further enhanced.

Figure 5:
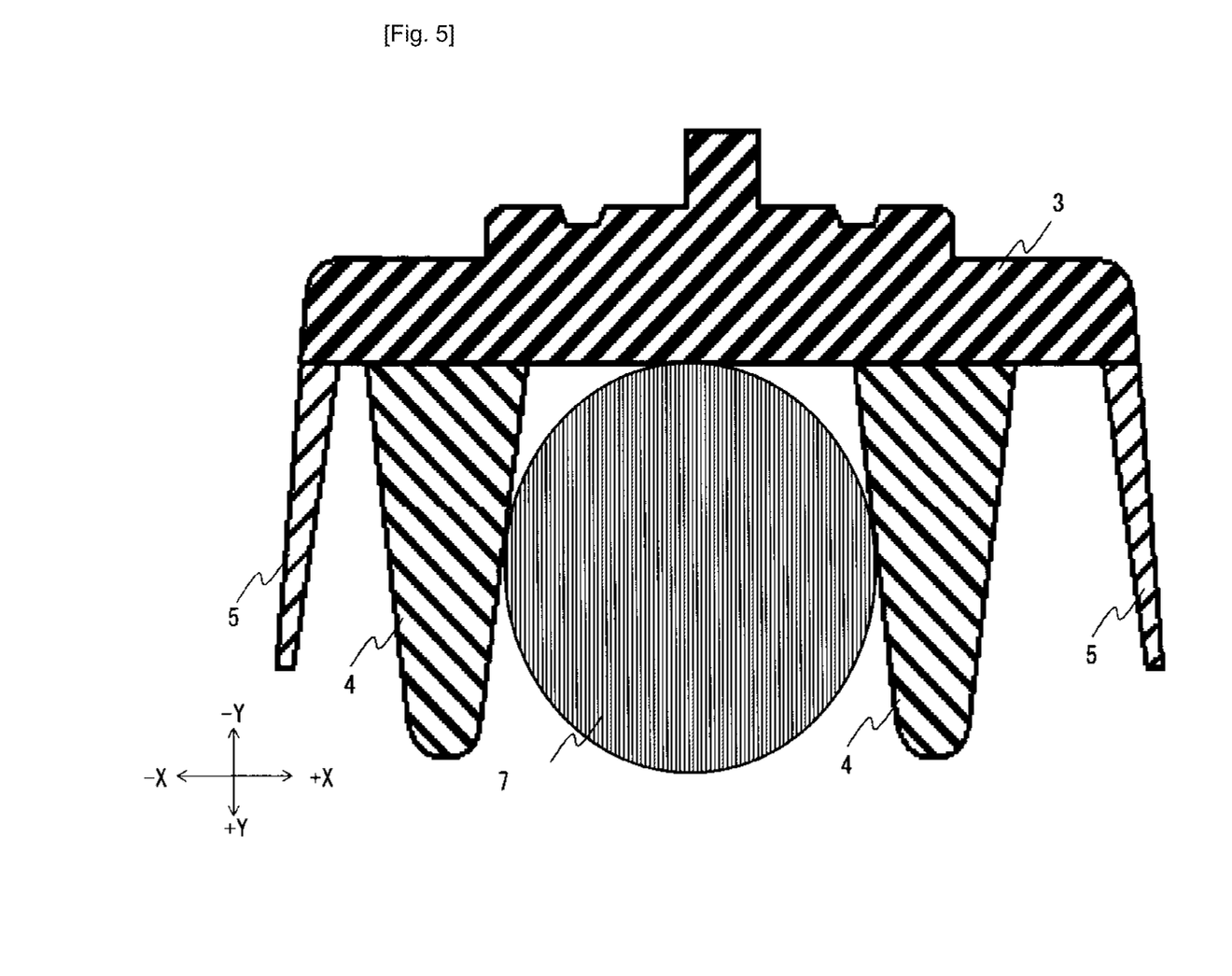
FIG. 5 is a sectional view of the electroencephalogram electrode 1 of Embodiment 1.

Although the configuration in which the electrode metal 2 is placed on the bottom portion 3 has been described referring to FIG. 3, the electrode configuration is not limited to this. For example, a configuration in which the bottom portion 3, the barb members 4, and the annular wall 5 are made of conductive materials, respectively may be employed. FIG. 5 is a sectional view (corresponding to FIG. 3) of the configuration.

In the configuration shown in FIG. 5, the electroencephalogram electrode 1 does not have the electrode metal 2. In the configuration, the bottom portion 3 and the connection member 8 are integrated with each other. Similarly with the configuration shown in FIG. 3, the bottom portion 3 is convex in the −Y direction. The bottom portion 3, the barb members 4, and the annular wall 5 are configured by conductive members. That is, the bottom portion 3, the barb members 4, and the annular wall 5 function also as an electrode for transmitting a biological signal of the subject to the electrocardiograph (external apparatus). Preferably, the conductive members are formed by highly conductive configurations (for example, a material which is obtained by mixing the above-described conductive carbon resin with silver or silver/silver chloride powder) so as to function as electrodes.

Figure 6:
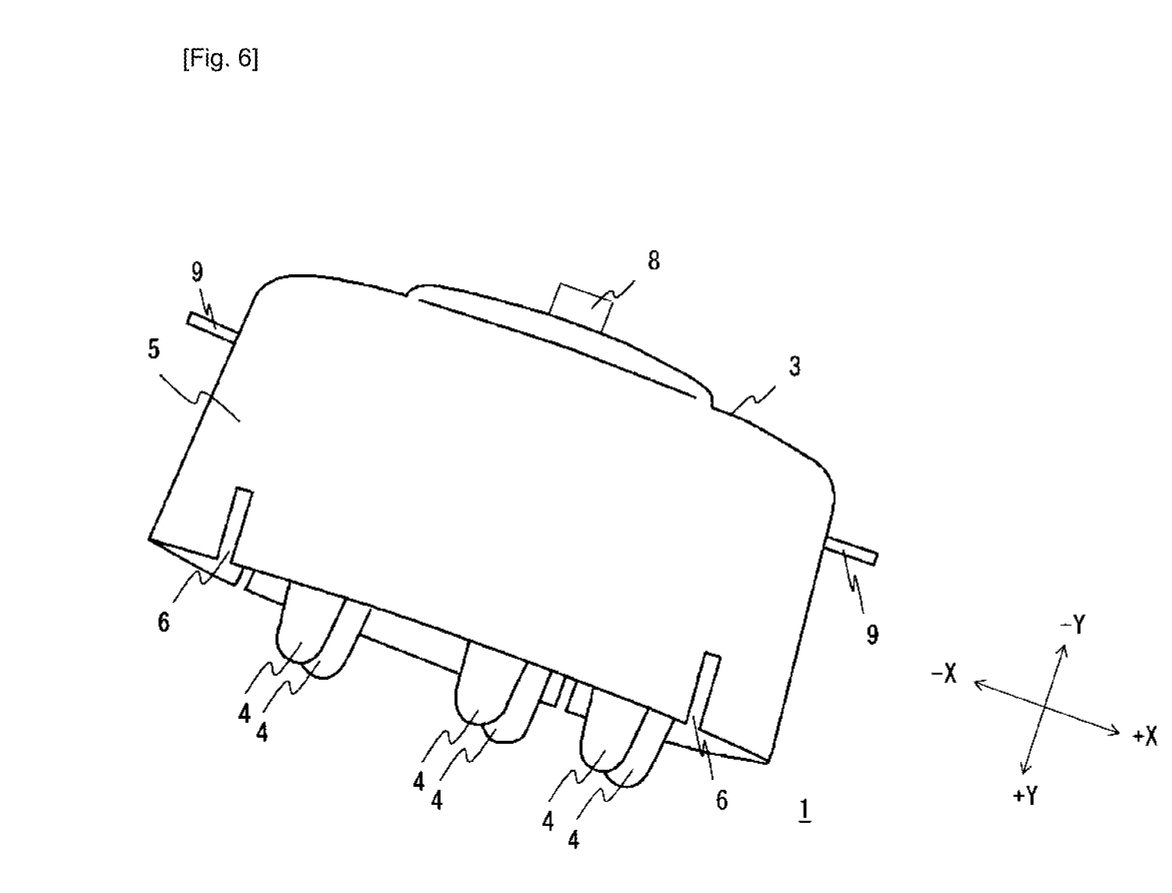
FIG. 6 is a perspective view showing the appearance of the electroencephalogram electrode 1 of Embodiment 1.

As shown in FIG. 6, projections 9 may be disposed on the annular wall 5. In the example of FIG. 6, two projections 9 are disposed at opposite positions of the annular wall 5, respectively. The operator holds the electrode while interposing the projections 9 between two fingers. Namely, the operator nips the projections 9, and does not directly press the flat portion (i.e., the portion where the conductive gel 7 is housed) of the annular wall 5. Therefore, it is possible to avoid a situation where the conductive gel 7 is caused to leak out by pressurization conducted by the operator, from occurring. The projections 9 are not required to be disposed on the annular wall 5, and may be disposed on the bottom portion 3. The number of the projections 9 is not particularly limited. When two projections are disposed, the electrode can be nipped so that the projections are interposed between two fingers.

Then, effects of the electroencephalogram electrode 1 of the embodiment will be described. In the above-described configuration, the conductive gel 7 is placed in the internal space surrounded by the annular wall 5. Therefore, it is possible to prevent the conductive gel 7 from leaking to the outside of the electroencephalogram electrode 1. Moreover, the barb members 4 fix the conductive gel 7 in a hooking manner. Therefore, it is possible to prevent the conductive gel 7 from dropping off during an operation such as attachment or detachment of the electroencephalogram electrode 1. That is, the above-described electroencephalogram electrode 1 can continue to stably hold the conductive gel 7 at a predetermined position for a long period of time.

Embodiment 2

The electroencephalogram electrode 1 of Embodiment 2 is characterized in that the annular wall 5 can be folded upon pressurization. With respect to the electroencephalogram electrode 1 of the embodiment, hereinafter, points different from Embodiment 1 will be described.

Figure 7A:
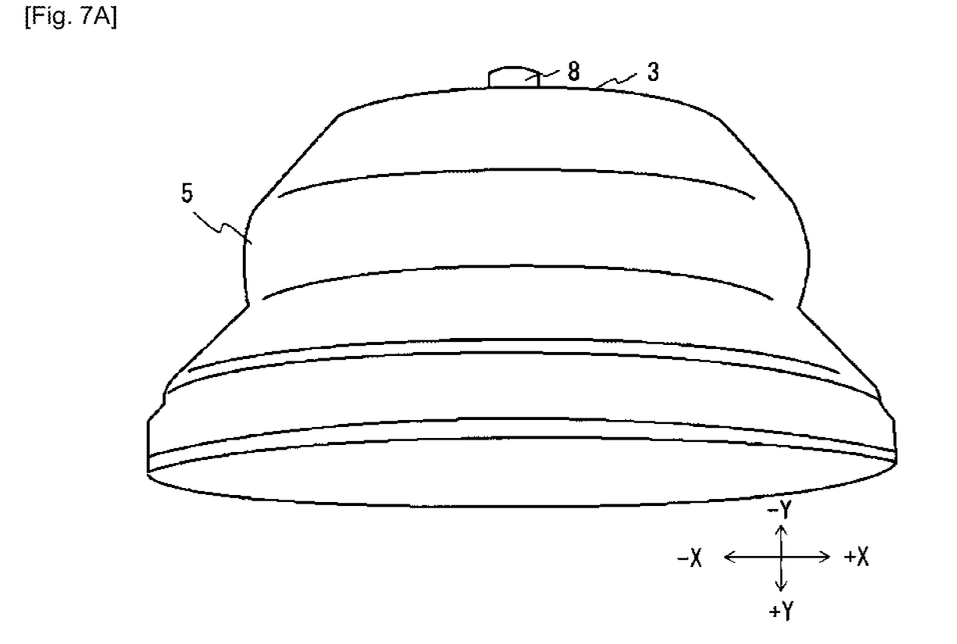
FIG. 7A is a perspective view showing the appearance of an electroencephalogram electrode 1 of Embodiment 2.
Figure 7B:
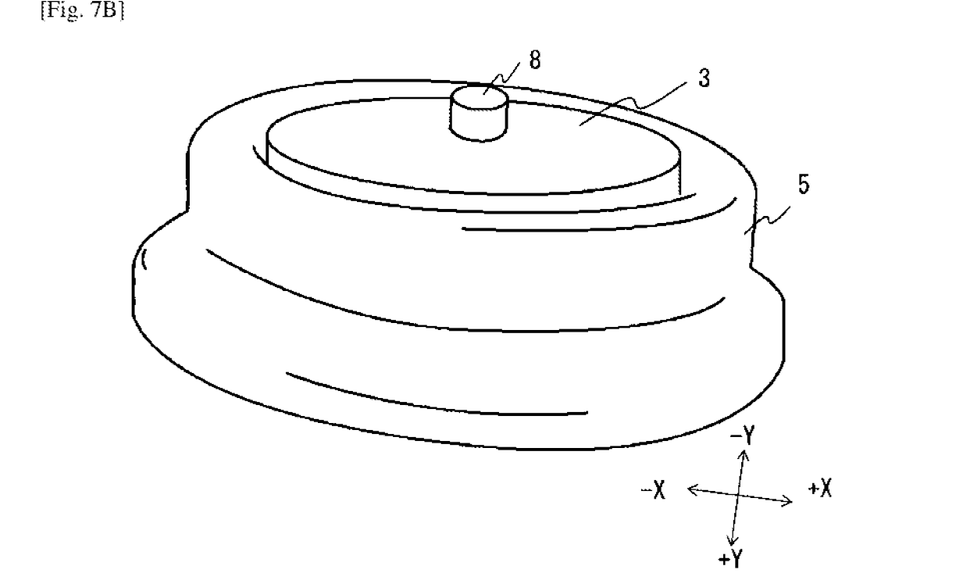
FIG. 7B is a perspective view showing the appearance of the electroencephalogram electrode 1 of Embodiment 2.

FIGS. 7A and 7B are perspective views showing the appearance of the electroencephalogram electrode 1 of the embodiment. As shown in FIG. 7A, the annular wall 5 has a step-like shape (shape including a plurality of steps). When the electroencephalogram electrode 1 is to be attached to the head of the subject, the operator pressurizes (presses) the electrode from the −Y direction toward the −Y direction. A part of the steps constituting the annular wall 5 is deformed by the pressurization so as to be folded. FIG. 7B shows the folded shape.

In the example of FIG. 7B, the annular wall 5 is folded in such a manner that the uppermost step portion of the annular wall 5 is housed in the next upper step. When the folding is performed in this way, the electrode metal 2 (not clearly shown in FIG. 7B) and the connection member 8 are moved so as to approach the head of the subject.

Then, an example of the cross-sectional structure of the electroencephalogram electrode 1 will be described with reference to FIG. 8. As illustrated, the annular wall 5 is outward flared to form the step-like shape. In the annular wall 5, the vicinity of the point where the angle is changed is the portion which is deformed in the folding process. The other configuration is approximately identical with that of FIG. 3.

Figure 8:
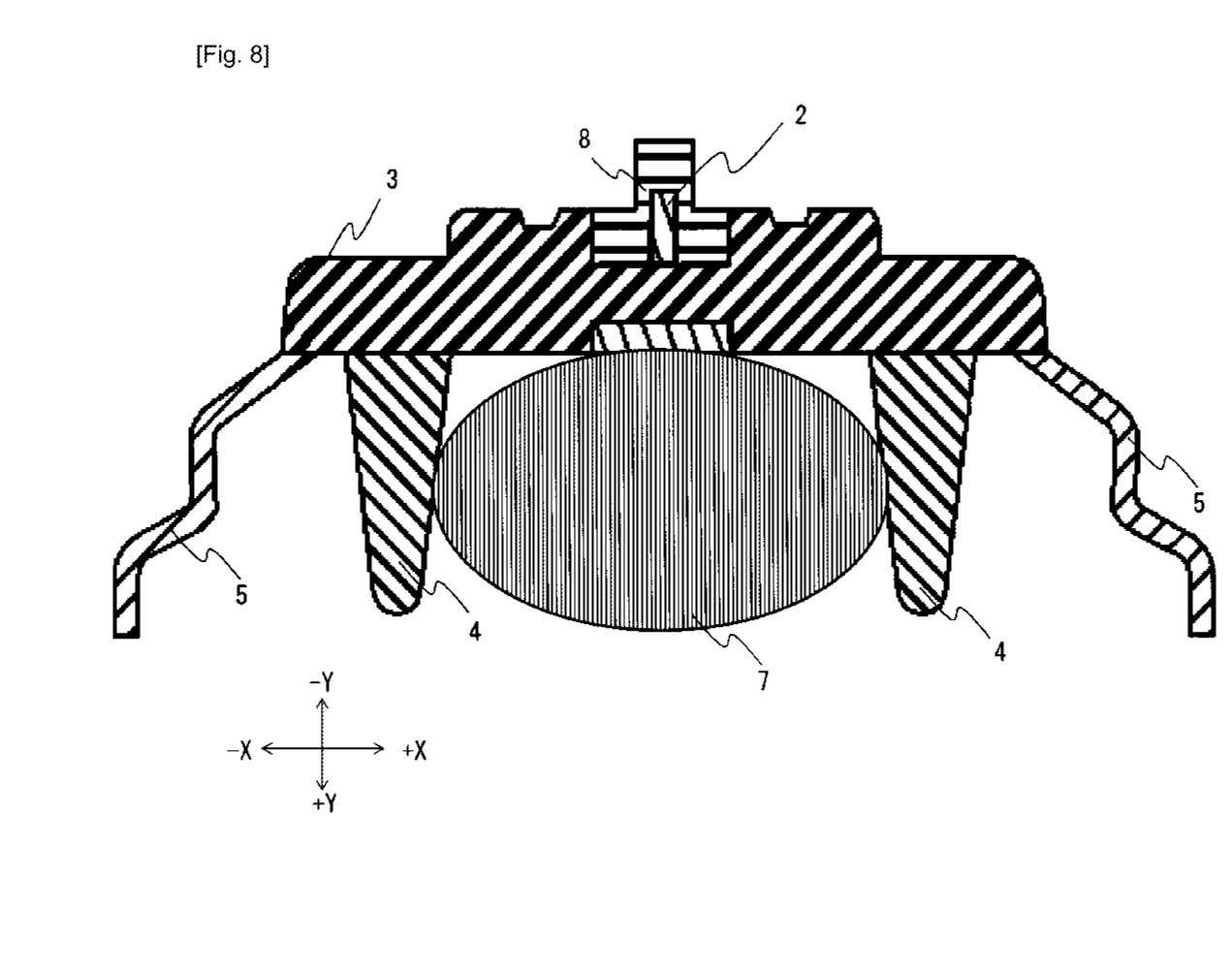
FIG. 8 is a sectional view of the electroencephalogram electrode 1 of Embodiment 2.

The example of FIG. 8 is illustrated so that the height (length in the Y-axis direction) of the barb members 4 is smaller than the height (length in the Y-axis direction) of the annular wall 5. This configuration is employed in consideration of the folding of the annular wall 5. It is a matter of course that a configuration in which the height of the barb members 4 is larger than that of the annular wall 5 is possible.

The amount of the conductive gel 7 shown in FIG. 8 is a mere example. Alternatively, the conductive gel 7 may be poured into the space in the annular wall 5 without forming any gap. In the configuration of FIGS. 7A and 7B, the slits 6 shown in FIG. 1 may be disposed.

Also in the embodiment, the bottom portion 3, the barb members 4, and the annular wall 5 may be configured by a non-conductive material. Alternatively, the bottom portion 3, the barb members 4, and the annular wall 5 may be configured by a conductive material. Similarly with the electroencephalogram electrode 1 which is shown in FIG. 5, and in which the electrode metal 2 is not explicitly disposed, the annular wall 5 may have a step-like shape.

Then, effects of the electroencephalogram electrode 1 of the embodiment will be described. As described above, the electroencephalogram electrode 1 of the embodiment has the annular wall 5 which is foldable. The electroencephalogram electrode 1 is used while a part of the annular wall 5 is folded. When the folding is performed, the connection member 8 and the electrode metal 2 are moved so as to approach the head of the subject. Therefore, it is possible to acquire more surely a biological signal of the subject.

The embodiment also includes the annular wall 5 and the plurality of barb members 4. According to the configuration, the conductive gel 7 can continue to be stably held for a long period of time.

Although the invention conducted by the inventor has been specifically described based on the embodiments, the invention is not limited to the above-described embodiments, and it is a matter of course that various changes can be made without departing from the spirit of the invention.

In the examples of FIGS. 3 and 8, the conductive gel 7 is placed inside the annular wall 5. Alternatively, the conductive gel 7 may be placed in a state where the gel is packaged in a production step in order to prevent drying. The conductive gel 7 may be administered separately from the electroencephalogram electrode 1, and the doctor or the like may pour the gel before the use of the electroencephalogram electrode 1.

Embodiment 3

The electroencephalogram electrode 1 of Embodiment 3 is characterized in that the annular wall 5 is configured by a sponge. With respect to the electroencephalogram electrode 1 of the embodiment, hereinafter, points different from Embodiment 1 will be described.

Figure 9:
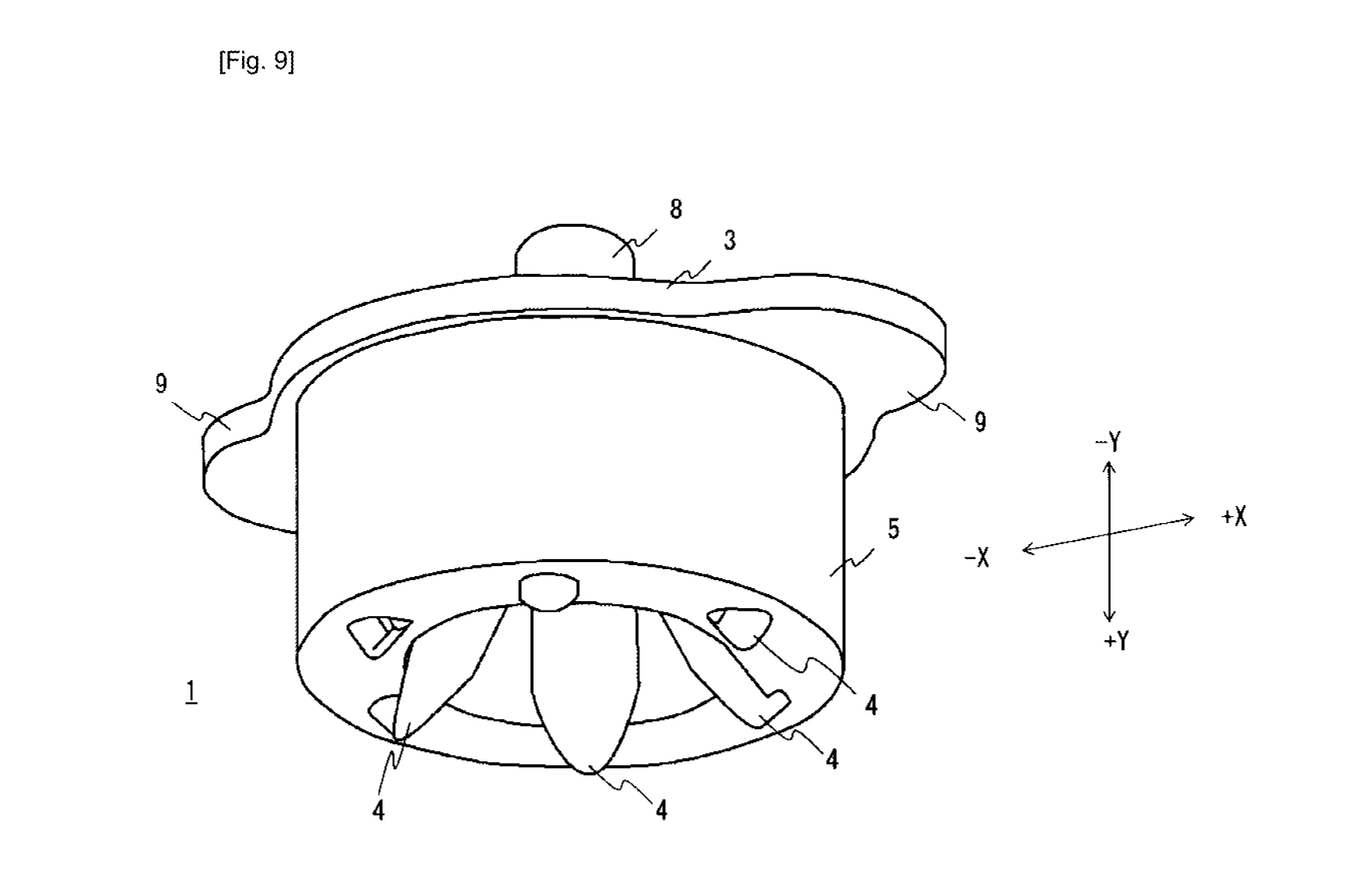
FIG. 9 is a perspective view showing the appearance of an electroencephalogram electrode 1 of Embodiment 3.

FIG. 9 is a perspective view showing the appearance of the electroencephalogram electrode 1 of the embodiment. The annular wall 5 is configured by a hollow columnar sponge having, for example, a thickness (thickness from the −X direction toward the +X direction) of about 5 mm, and a height (height from the −Y direction toward the +Y direction) of about 10 mm. In the embodiment, six barb members 4 are disposed. In the embodiment, the barb members 4 elongate from the bottom portion 3 toward the +Y direction, and also toward the outside (in the direction approaching the annular wall 5). Namely, the barb members 4 elongate while forming an angle so as to approach the annular wall 5 as more moving toward the +Y direction.

The barb members 4 may be made of a material (for example, a film-molded material or a non-conductive elastic material) which is so soft that, even when the members are in contact with the scalp of the subject, the members do not cause pain. The soft material may be coated with a conductive material. For example, the barb members 4 may have a configuration in which polyethylene terephthalate (PET) having elasticity is coated with silver or silver/silver chloride powder. The silver or silver/silver chloride powder is an example of a conductive material, and another material may be used. Although not illustrated, the conductive gel 7 is filled in the space surrounded by the barb members 4 and the bottom portion 3. The tip ends of the barb members 4 are configured so as to have a folded back portion. The folded back portions are hooked by the annular wall 5, whereby the barb members 4 are fixed in such a manner that the annular wall 5 is in contact with the bottom portion 3.

In the configuration of FIG. 9, two rounded projections 9 are disposed in the bottom portion 3. The projections 9 are nipped by the operator. The annular wall 5 is not directly pressed by the operator, and it is possible to avoid a situation where the conductive gel 7 flows out.

Figure 10:
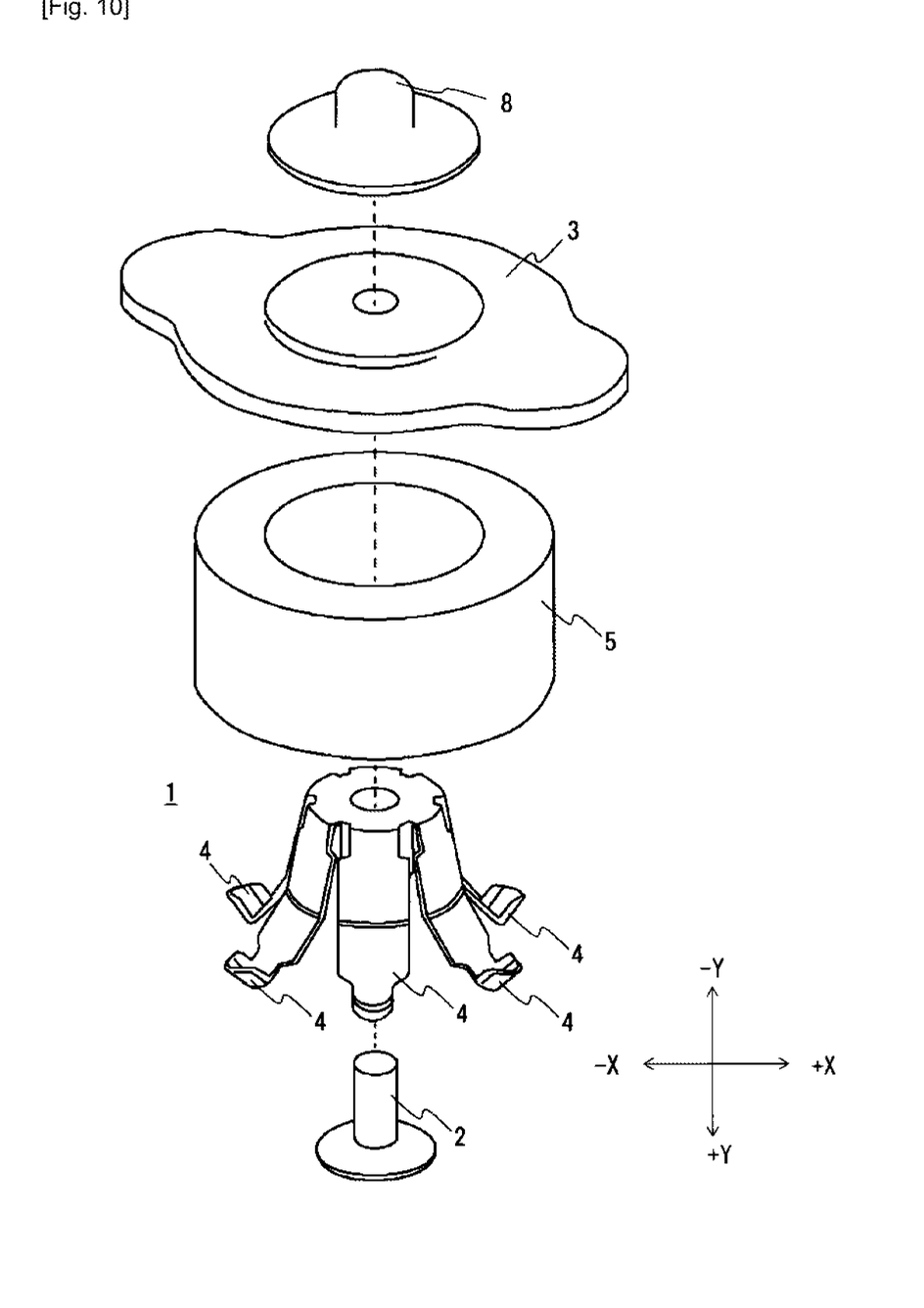
FIG. 10 is an exploded perspective view of the electroencephalogram electrode 1 of Embodiment 3.

FIG. 10 is an exploded perspective view of the electroencephalogram electrode 1 of the embodiment. The connection member 8, the bottom portion 3, the annular wall 5, the barb members 4, and the electrode metal 2 are sequentially arranged with starting from the −Y direction. In the embodiment, the plurality of barb members 4 are connected to the one bottom portion. The connection member 8 has a fitting portion (recess) into which the electrode metal 2 is fitted. The electrode metal 2 is configured by a material which is coated with, for example, silver/silver chloride. The connection member 8 is configured by a conductive material (for example, carbon). A through hole is formed in each of the bottom portion 3 and the barb members 4 (a bottom portion which is connected to the barb members). When the electrode metal 2 is fitted into the connection member 8 (a member having the connection member) in a state where the members are arranged as shown in FIG. 10, a state where the members are connected to one another (the state shown in FIG. 9) is attained. As a result, the conductivity in the range from the head of the subject to the connection member 8 is ensured. The folded back portions of the barb members 4 are hooked by a part of the annular wall 5, and the barb members 4 are fixed in such a manner that the annular wall 5 is in contact with the bottom portion 3.

As described above, the barb members 4 elongate in the +Y direction (approximate contact direction with respect to the subject), and have a shape which further approaches the annular wall 5 as more elongating (in other words, a shape which is outward flared).

The electroencephalogram electrode 1 is pressed toward the +Y direction, and contacted with the scalp of the subject. In this case, the annular wall 5 formed by a sponge collapsingly bends, and the barb members 4 bend so as to be flared toward the outside (side of the annular wall 5) (in other words, collapse). Therefore, the conductive gel 7 is in close contact with the head of the subject, and the electrode metal 2 incorporated in the bottom portion 3 is moved so as to approach the scalp. As a result, the electroencephalogram of the subject can be stably acquired.

Also in the electroencephalogram electrode 1 of the embodiment, the annular wall 5 prevents the conductive gel 7 from flowing out, and the barb members 4 holdingly fix the conductive gel 7. Therefore, the conductive gel 7 can be continued to be stably held.

The annular wall 5 in the embodiment is formed by a sponge, and the barb members 4 have the configuration in which the members are coated with a conductive material. Even when these materials are in contact with the head of the subject, the pressure applied to the head of the subject is low. Therefore, the electroencephalogram measurement can be stably performed for a long period of time.

Figure 11:
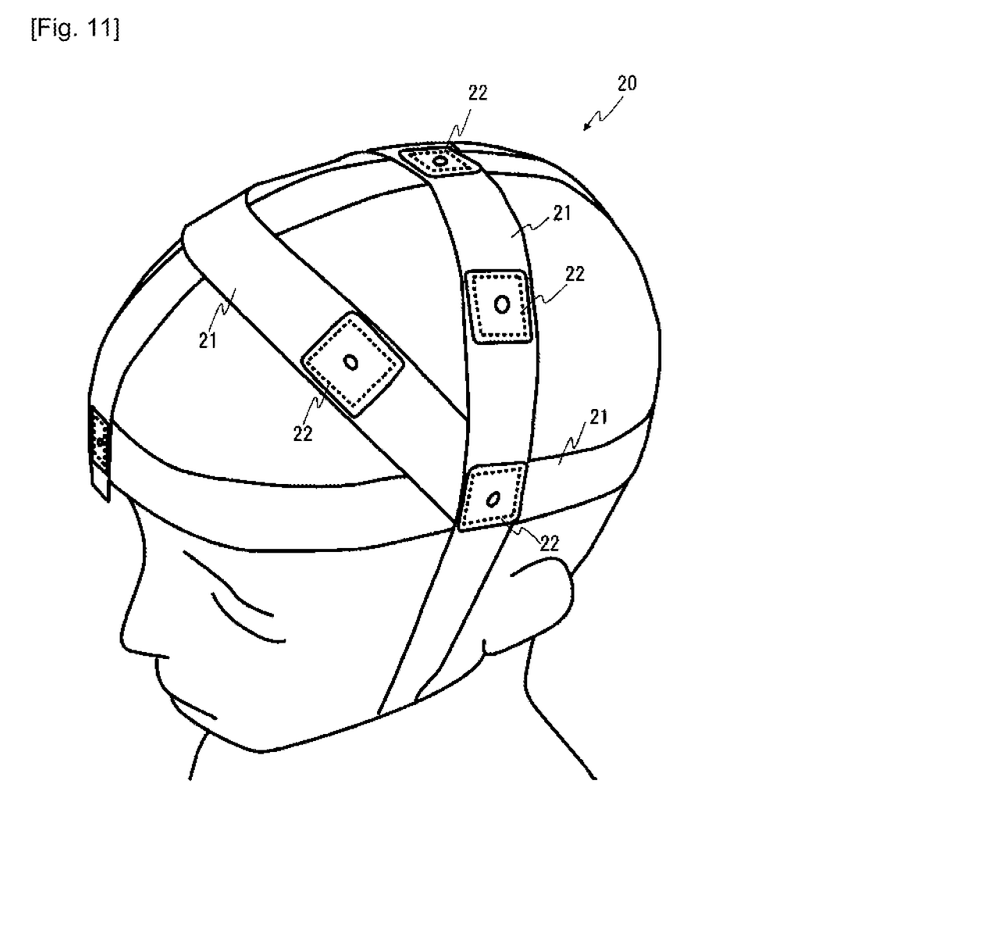
FIG. 11 is a view showing an example of a headband in which electroencephalogram electrodes 1 of Embodiment 1 (or Embodiment 2 or 3) are placed.

Finally, an example of placement of the electroencephalogram electrode 1 of the invention on the scalp will be described with reference to FIGS. 11 and 12. FIG. 11 is a conceptual view showing an example of a headband for placing electroencephalogram electrodes 1. FIG. 11 shows a mere example, and a headband (harness for electroencephalogram electrodes) of any kind may be used as far as electroencephalogram electrodes 1 can be fixed.

A headband 20 has a support member 21 which is formed by sawing together a plurality of stretching bands, and a plurality of electrode fixing portions 22. The electrode fixing portions 22 are disposed at positions which are defined in the International 10/20 system, respectively. Through holes for attaching an electroencephalogram electrode are disposed in the plurality of electrode fixing portions 22, respectively.

The electroencephalogram electrodes 1 are attached to the electrode fixing portions 22, respectively. FIG. 12 shows a placement example. The connection member 8 of each of the electroencephalogram electrodes 1 is passed through the through hole of the corresponding electrode fixing portion 22, thereby causing the connection member 8 to be exposed to the outside of the support member 21. A cord of the electrocardiograph is connected to the connection member 8 (for example, the connection member 8 is nipped by a crocodile clip which is attached to the tip end of the cord of the electrocardiograph), whereby the electroencephalogram electrode 1 and the electrocardiograph are connected to each other.

Figure 12:
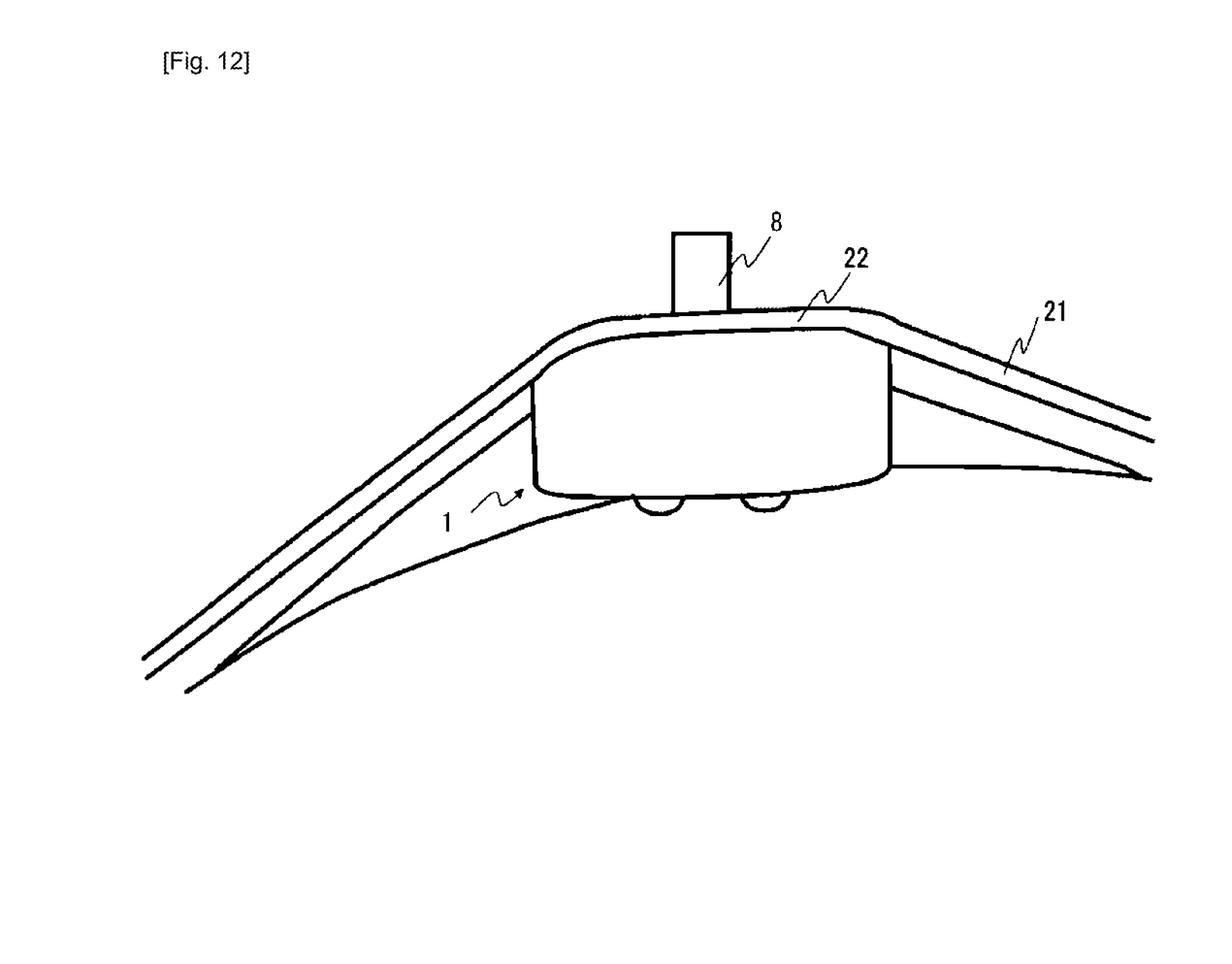
FIG. 12 is a view showing a placement example of the electroencephalogram electrode 1 of Embodiment 1.

FIG. 12 shows the example of attachment of the electroencephalogram electrode 1 of Embodiment 1. The electroencephalogram electrodes of Embodiments 2 and 3 can be similarly attached. In the case where the electroencephalogram electrode of Embodiment 2 is to be attached, when the electrode fixing portion 22 is pressed after the electroencephalogram electrode 1 is attached, a part of the annular wall 5 is folded.

According to the above-described configuration, the conductive gel is placed in the internal space surrounded by the annular wall. Therefore, it is possible to prevent the conductive gel from leaking to the outside of the electroencephalogram electrode. Moreover, the barb members fix the conductive gel in a hooking manner. Therefore, it is possible to prevent the conductive gel from dropping off during an operation such as attachment or detachment of the electroencephalogram electrode. Furthermore, the annular wall reduces an area where the included conductive gel is in contact with the ambient air, and the conductive gel can be prevented from drying. Because of these functions, the electroencephalogram electrode can continue to stably hold the conductive gel.

The present application is based on Japanese Patent Application No. 2015-032384 filed on Feb. 23, 2015, the contents of which are incorporated herein by way of reference.

INDUSTRIAL APPLICABILITY

According to the invention, it is possible to provide an electroencephalogram electrode in which gel itself can be held at a predetermined position for a long period of time.

The invention claimed is:

1. An electroencephalogram electrode comprising:
   conductive gel;
   a bottom portion on which a connection member is placed, wherein the connection member is configured to supply a biological signal acquired from a subject through the conductive gel to an external apparatus;
   an annular wall which annularly extends from the bottom portion in a contact direction with respect to the subject; and
   a plurality of barb members which are disposed in a holding space for the conductive gel that is located inside the annular wall, which are configured to hold the conductive gel interposed among the plurality of barb members when the electroencephalogram electrode is attached to the subject, and which elongate from the bottom portion in the contact direction,
   wherein the annular wall surrounds the plurality of barb members and comprises a slit configured to deform and cause the annular wall to bend so that a tip end of the annular wall that is disposed opposite to the bottom portion expands outward when the electroencephalogram electrode is attached to the subject,
   wherein the annular wall extends so that the tip end expands outward, and the slit is formed in a portion of the annular wall including the tip end and elongates in the contact direction so that a tip end of the slit expands outward before the electroencephalogram electrode is attached to the subject, and
   wherein a width of at least a part of each of the plurality of barb members in a width direction perpendicular to the contact direction is larger than a width of the slit in the width direction.

2. The electroencephalogram electrode according to claim 1, wherein a height of the plurality of barb members is larger than a height of the annular wall.

3. The electroencephalogram electrode according to claim 1, wherein the annular wall has a shape which is caused to bend by pressurization.

4. The electroencephalogram electrode according to claim 1, wherein the annular wall, the plurality of barb members, and the bottom portion comprise a conductive material.

5. The electroencephalogram electrode according to claim 4, wherein the conductive material is conductive carbon resin.

6. The electroencephalogram electrode according to claim 4, wherein the conductive material is produced by mixing a conductive carbon resin with silver or silver/silver chloride powder.

7. The electroencephalogram electrode according to claim 1, wherein the annular wall, the plurality of barb members, and the bottom portion comprise a non-conductive material.

8. The electroencephalogram electrode according to claim 1, wherein the annular wall has a step-like shape which is foldable.

9. The electroencephalogram electrode according to claim 1, wherein the annular wall has a shape which is outward flared.

10. The electroencephalogram electrode according to claim 1, wherein the annular wall or the bottom portion includes a projection.

11. The electroencephalogram electrode according to claim 1, wherein the annular wall is configured as a sponge.

12. The electroencephalogram electrode according to claim 11, wherein the plurality of barb members have a configuration which is outwardly flared.

13. The electroencephalogram electrode according to claim 11, wherein the plurality of barb members have a configuration in which polyethylene terephthalate is coated with a conductive material.

14. The electroencephalogram electrode according to claim 1, wherein the plurality of barb members fix the conductive gel in a hooking manner.

15. The electroencephalogram electrode according to claim 1, wherein an inner surface of the annular wall is spaced apart from the plurality of barb members along an entire height of the annular wall.

16. The electroencephalogram electrode according to claim 1, wherein each of the plurality of barb members has a tapered shape.

17. The electroencephalogram electrode according to claim 1, wherein the slit is formed in the portion of the annular wall and elongates in the contact direction without reaching the bottom portion.

18. An electroencephalogram electrode comprising:
a bottom portion on which a connection member is placed, wherein the connection member is configured to supply a biological signal acquired from a subject through conductive gel, to an external apparatus;
an annular wall which annularly extends from the bottom portion in a contact direction with respect to the subject; and
a plurality of barb members which are disposed in a holding space for the conductive gel that is located in an interior of the annular wall, which are configured to hold the conductive gel interposed among the plurality of barb members when the electroencephalogram electrode is attached to the subject, and which elongate from the bottom portion in the contact direction,
wherein the annular wall surrounds the plurality of barb members and comprises a slit configured to deform and cause the annular wall to bend so that a tip end of the annular wall that is disposed opposite to the bottom portion expands outward when the electroencephalogram electrode is attached to the subject,
wherein the annular wall extends so that the tip end expands outward, and the slit is formed in a portion of the annular wall including the tip end and elongates in the contact direction so that a tip end of the slit expands outward before the electroencephalogram electrode is attached to the subject, and
wherein a width of at least a part of each of the plurality of barb members in a width direction perpendicular to the contact direction is larger than a width of the slit in the width direction.

19. The electroencephalogram electrode according to claim 18, wherein the plurality of barb members fix the conductive gel in a hooking manner.

20. The electroencephalogram electrode according to claim 18, wherein the slit is formed in the portion of the annular wall and elongates in the contact direction without reaching the bottom portion.

* * * * *